(12) United States Patent
Hannu-Kuure et al.

(10) Patent No.: US 7,393,560 B2
(45) Date of Patent: Jul. 1, 2008

(54) ORGANO-METAL COMPOUNDS

(75) Inventors: Milja Hannu-Kuure, Oulu (FI); Ari Kärkkäinen, Oulu (FI)

(73) Assignee: Braggone OY, Oulu (FI)

( * ) Notice: Subject to any disclaimer, the term of this patent is extended or adjusted under 35 U.S.C. 154(b) by 0 days.

(21) Appl. No.: 11/415,521

(22) Filed: May 2, 2006

(65) Prior Publication Data

US 2006/0263621 A1   Nov. 23, 2006

Related U.S. Application Data

(60) Provisional application No. 60/677,169, filed on May 3, 2005.

(51) Int. Cl.
*B05D 3/02* (2006.01)
*C08G 79/00* (2006.01)
*C07F 7/00* (2006.01)

(52) U.S. Cl. .............................. 427/226; 528/9; 556/89; 556/95; 556/96

(58) Field of Classification Search .................. 556/89, 556/95, 96; 427/226; 528/9
See application file for complete search history.

(56) References Cited

OTHER PUBLICATIONS

Pikina et al., Chemical Abstracts, abstract No. 41342, vol. 33 (1939).*

* cited by examiner

*Primary Examiner*—Porfirio Nazario Gonzale
(74) *Attorney, Agent, or Firm*—McCormick, Paulding & Huber LLP

(57) ABSTRACT

Organo-tin compound having the formula I:

$$[R-(Y)_a]_b-SnX_{4-b}$$

wherein R stands for a polycyclic hydrocarbyl residue which optionally carries one or several substituents; Y stands for a bivalent linker group; X represents a hydrolysable group; a is an integer 0 or 1; and b is an integer 1 or 2. The preferably stands for an unsubstituted or substituted fused hydrocarbon ring system selected from naphthalene, anthracene, phenanthrene, and pentacene. The novel compounds are useful for producing polymers which can be employed as thin film materials in optoelectronic devices.

17 Claims, No Drawings

ORGANO-METAL COMPOUNDS

Cross Reference To Related Application

This application claims the benefit of U.S. Provisional Application 60/677,169 filed May 3, 2005, which is incorporated herein by reference.

BACKGROUND OF THE INVENTION

1. Field of the Invention

The present invention relates to organo-metal compounds. In particular, the present invention relates to novel organo-tin compounds useful as monomers for the production of novel tin containing polymers. The present invention also relates to processes for producing the novel compounds and the methods for obtaining the novel polymers.

2. Description of Related Art

Electronic and optical materials have been produced using silicon oxide polymers, e.g., silicones and siloxanes. These polymers are conventionally made via condensation of silicon precursors, said condensation step involving hydrolysis of hydrolysable (leaving) groups attached to the silicon atoms. These leaving groups are typically selected from halogen atoms and alkoxy groups. The silicon precursors may also comprise covalently bonded organic groups. Representative examples of such organic groups include, for example, alkyl, aryl and polycyclic aromatic moieties. The siloxane compositions have been found to be useful in optoelectronic applications, such as in waveguide structures and components thereof.

It has also been recently observed that when polycyclic aromatic groups, such as pentacene, are attached to the silicone or siloxane matrix, the matrix becomes photo- and electroluminescent. It appears that luminescent organic components attached to the siloxane are capable of improving their stability against thermal and environmental aging.

However, siloxane based organic hybrid materials of the above kind do not always perform satisfactorily when used as polymeric host or matrix materials in optoelectronic applications. This is the case in particular when charge transfers (such electron and hole injections) are required for the device functionality as in electroluminescent, photodiode and solar cell components due their inherent dielectric nature.

SUMMARY OF THE INVENTION

It is an object of the present invention to eliminate at least some of the drawbacks of the prior art and to provide novel organo-metal hybrid materials, which are compatible with optoelectronic devices.

It is another object of the invention to provide novel monomers, which can be polymerized to produce polymeric organo-metal hybrid materials.

It is a third object of the invention to provide a process of synthesizing novel organo-metal monomers.

These and other objects, together with the advantages thereof over known methods and compositions, are achieved by the present invention as hereinafter described and claimed.

The present invention is based on the idea that by replacing the silicon atom of organic hybrid materials with tin, materials are obtained which have electronic and optoelectronic properties that match better the corresponding properties of components conventionally used in optoelectronic devices, such as electroluminescent components, photodiodes and solar cells. Typically, these devices are provided with electrodes, at least one of which, typically the anode, is comprised of a mixed tin oxide, such as indium tin oxide (abbreviated "ITO"). Thus, the present invention provides a group of novel organo-tin components and polymer compositions made from these components and their applications.

Further, in order to ensure a sufficiently high thermal stability of the polymer matrices, in the organo-tin materials, organic electrooptic moieties are incorporated, covalently bonded to the matrix. The organo-tin monomers therefore comprise at least one substituted or non-substituted polycyclic aromatic group attached to a tin atom and at least one hydrolysable group.

The novel monomers correspond to formula I:

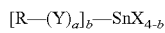

$$[R-(Y)_a]_b-SnX_{4-b} \qquad I$$

wherein
R stands for a polycyclic hydrocarbyl residue which optionally carries one or several substituents;
Y stands for a bivalent linker group;
X represents a hydrolysable group;
a is an integer 0 or 1; and
b is an integer 1 or 2.

The monomers can be prepared by, e.g., the steps of:
reacting a halogenide of a polycyclic hydrocarbon organic compound with magnesium in an organic solvent in order to form a reagent having the formula RMgHal, in which R has the same meaning as above and Hal stands for a halogen;
mixing the reagent with a tin halide to form a reaction mixture;
reacting the reagent with the tin halide to form a compound of formula I in the reaction mixture; and
recovering the compound of formula I from the reaction mixture.

The monomers of formula I are valuable organo-tin precursors for polymeric organo-tin (oxide) materials, obtainable for example by hydrolysis and condensation polymerization of the precursors by methods known per se.

This composition can be used in a method of coating substrates, comprising the steps of
applying on the surface of the substrate a solution of an organo-tin precursor or polymer of the above kind,
forming a thin layer on the surface,
removing the solvent of the solution and
subjecting the film heat processing in order to cure the thin layer into a film.

More specifically, the present organo-tin compounds or precursors are mainly characterized by what is stated in the characterizing part of claim 1.

The present polymers are characterized by what is stated in the characterizing part of claim 13.

The method of coating substrates is characterized by what is stated in the characterizing part of claim 17.

The present invention provides considerable advantages. Thus, the novel monomers and, in particular, polymers manufactured therefrom have an excellent thermal stability and good optoelectronic properties which makes them particularly suitable as components in various luminescent devices. Compared with conventional silicon dioxide based materials, the present polymeric organo-tin materials have higher refractive indices.

DETAILED DESCRIPTION OF THE INVENTION

By "polycyclic aromatic groups" we mean aromatic compounds wherein at least two aryl groups are fused together, such as naphthalene, anthracene, phenanthrene, pentacene or similar. Generally, the polycyclic group is selected from fused polycyclic hydrocarbons comprises 2 to 6 alicyclic, heterocyclic or, in particular, aromatic rings having 5 to 7 members, preferably 6 carbon atoms.

By "hydrolysable group" we mean halogen (chlorine, fluorine, bromine), alkoxy (in particular $C_{1-10}$ alkoxy, such as methoxy, ethoxy, propoxy, or butoxy) or hydrogen or any other group that can easily be cleaved off the monomer during condensation polymerization.

The polycyclic aromatic group can be attached to the tin directly by a carbon-tin bond, preferably a covalent bond, or via a linker group. Typically, the linker comprises 1 to 10 carbon atoms. Examples of suitable linker groups Y include alkylene, alkenylene and alkynylene groups. "Alkylene" groups generally have the formula —$(CH_2)_r$— in which r is an integer 1 to 10. One or both of the hydrogens of at least one unit —$CH_2$— can be substituted by any of the substituents mentioned below. The "alkenylene" groups correspond to alkylene residues, which contain at least one double bond in the hydrocarbon backbone. If there are several double bonds, they are preferably conjugated. "Alkynylene" groups, by contrast, contain at least one triple bond in the hydrocarbon backbone corresponding to the alkylene residues.

The polycyclic aromatic groups and the linker groups can be unsubstituted or substituted. The substituents are preferably selected from the group of fluoro, bromo, $C_{1-10}$-alkyl, $C_{1-10}$-alkenyl, $C_{6-18}$-aryl, acryl, epoxy, carboxyl and carbonyl groups.

As briefly discussed above, we have found that it is advantageous in optoelectronic devices, device layers and structures to use materials and compositions that match better the materials of the other parts of the device, for example the ITO (indium tin oxide) in the anode, as far as their electronic and optoelectronic properties are concerned, than for example siloxane materials do. It is preferred to use materials, which are based on organo-metal compositions, which contain the same kinds of metal atoms as the components of the device.

By further incorporating organic electrooptic moieties by covalent bonds to the matrix, improved thermal stability is reached compared with conventional organic polymer matrices.

The present organo-tin compounds can be polymerized to form polymeric tin dioxides. These polymers are particularly attractive as matrices and hosts for organic components because they have excellent optoelectronic properties. In the art, organo-tin monomers, such as phenyl trichlorotin and divinyl dichlorotin, are known. However, these monomers cannot be used for forming for luminescent devices as such since they do not function as emissive and absorptive materials in wavelength range of visible light. The present monomer molecules and polymers, having polycyclic aromatic compounds attached covalently to the tin atom or tin oxide polymer matrix, have not been suggested before. The attachment of such molecules to tin atom and in particular to hydrolysable tin atom is crucial in forming electrooptical devices, such as emitters, displays, detectors and solar cells.

The present organo-tin compound generally correspond to the formula I:

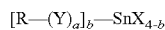

$$[R-(Y)_a]_b-SnX_{4-b} \quad \text{I}$$

wherein
R stands for a polycyclic hydrocarbyl residue which optionally carries one or several substituents;
Y stands for a bivalent linker group;
X represents a hydrolysable group;
a is an integer 0 or 1; and
b is an integer 1 or 2.

The hydrocarbyl residue typically comprises a fused polycyclic hydrocarbon comprises 2 to 6 alicyclic, heterocyclic or aromatic rings having 5 to 7 members. Y is an alkylene, alkenylene, or alkynylene chain comprising 1-10 carbons. X stands for halogen, $C_{1-10}$-alkoxy or hydrogen.

Both R and Y in the above definitions can be, independently of other Rsk and Ys and independently of the Rs and Ys, substituted by one or several substituents selected from fluoro, bromo, $C_{1-10}$-alkyl, $C_{1-10}$-alkenyl, $C_{6-18}$-aryl, acryl, epoxy, carboxyl and carbonyl groups.

In the above formulas, the $C_{1-10}$-alkyl groups can be linear or branched or cyclic alkyl groups, optionally bearing at least one halogen substituent, such as a chloro, bromo or fluoro substituent. In particular, the alkyl group is a lower alkyl containing 1 to 6 carbon atoms, which optionally bears 1 to 3 substituents selected from methyl and halogen. Methyl, ethyl, n-propyl, i-propyl, n-butyl, i-butyl and t-butyl are particularly preferred.

The $C_{1-10}$-alkenyl groups can comprise ethylenically unsaturated groups, which have a double bond located at position 2 or higher with respect to the Sn atom or the carbon atom of the backbone. A preferred example of the alkenyl groups comprises vinyl. Branched alkenyl is preferably branched at the alpha or beta position with one and more, preferably two, $C_1$ to $C_6$ alkyl, alkenyl or alkynyl groups. The alkenyl groups can be substituted with at least one halogen substituent, such as a chloro, bromo or fluoro substituent.

Alkynyl contains an ethylinic group, i.e. two carbon atoms bonded with triple bond. It is preferably located at position 2 or higher, related to the Sn atom or the carbon atom of the backbone to which it is attached. Branched alkynyls are preferably branched at the alpha or beta position with one and more, preferably two, $C_1$ to $C_6$ alkyl, alkenyl or alkynyl groups. The alkynyl groups can be substituted with at least one halogen substitutent, such as a chloro, bromo or fluoro substituent.

Preferred embodiments of the aryl groups include phenyl, which optionally bears 1 to 5 substituents selected from halogen, alkyl or alkenyl on the ring, or naphthyl, which optionally bear 1 to 11 substituents selected from halogen alkyl or alkenyl on the ring structure, the substituents being optionally fluorinated (including per-fluorinated or partially fluorinated). Other substituents include acryl, epoxy, vinyl, carboxyl and carbonyl groups. Reactive functional substituents will provide for some cross-linking during polymerization of the monomers, forming bridges between adjacent polycyclic structures.

"Alkoxy groups" have the formula $R^4O$—, wherein $R^4$ stands for an alkyl as defined above. The alkyl residue of the alkoxy groups can be linear or branched. Typically, the alkoxy groups are comprised of lower alkoxy groups having 1 to 6 carbon atoms, such as methoxy, ethoxy and t-butoxy groups.

In some specific examples of compounds according to the above general formula, the hydrocarbyl residue stands for an unsubstituted or substituted fused hydrocarbon ring system selected from naphthalene, antracene, phenanthrene, and pentacene.

Falling within the general formula I, there are some preferred embodiment. The first embodiment comprises compounds of formula II:

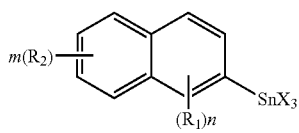

wherein
X is hydrolysable group,
R$_1$ and R$_2$ are independently selected from hydrogen, fluorine, bromine, C$_{1-10}$-alkyl, C$_{1-10}$-alkenyl, C$_{6-18}$-aryl, acryl, epoxy, carboxyl and carbonyl groups, two substituents R$_1$ being capable of forming a 5 to 7 membered ring together with the adjacent carbon ring atoms to which they are attached;
m is an integer 0 to 4; and
n is an integer 0 to 3.

Specific examples of representative embodiments include naphthalene trichlorotin having the formula IIa

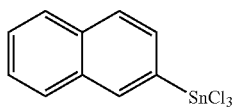

naphthalene trimethoxytin having the formula IIb

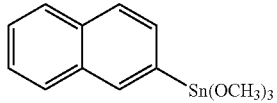

naphthalene triethoxytin having the formula IIc

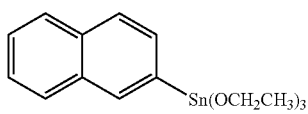

and
1,4-diphenyl naphthalene 3-trichlorotin having the formula IId

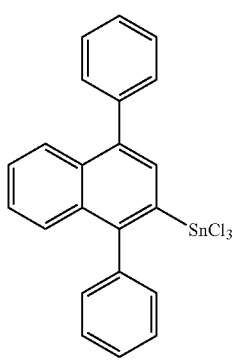

Another embodiment falling within the general formula I are the compounds a) having the formula III:

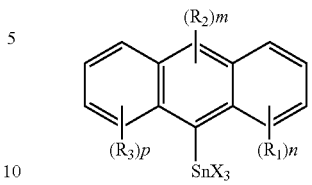

wherein X, R$_1$ and R$_2$ have the same meaning as above in connection with formula II, R$_3$ stands independently of R$_1$ and R$_2$ for hydrogen, fluorine, bromine, C$_{1-10}$-alkyl, C$_{1-10}$-alkenyl, C$_{6-18}$-aryl, acryl, epoxy, carboxyl and carbonyl, m is 0 or 1, n is an integer 0 to 4 and p is an integer 0 to 4, and b) the corresponding phenantrene derivatives thereof.
These are illustrated by:

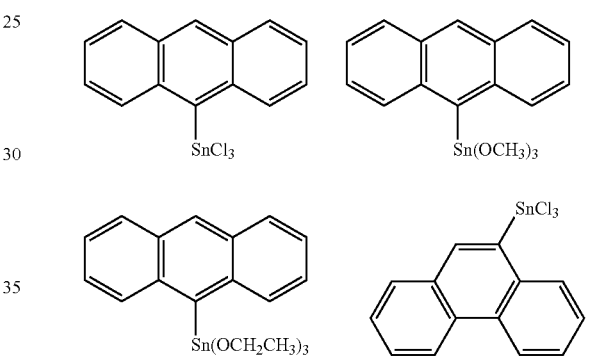

A third preferred embodiment comprises compounds having the formula IV:

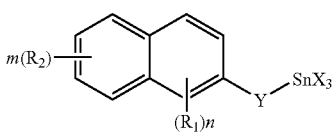

wherein X, R$_1$, R$_2$, Y, n and m have the same meaning as above in connection with formula II.

These are illustrated by

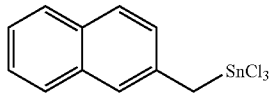

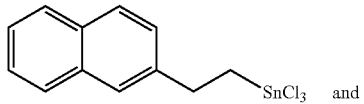 and

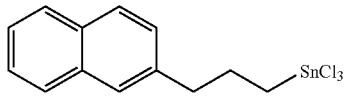

Further embodiments include compounds having formulas

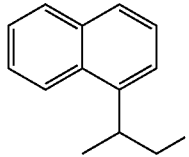 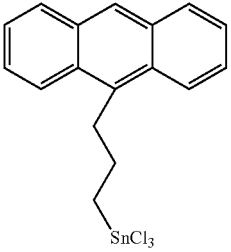 and

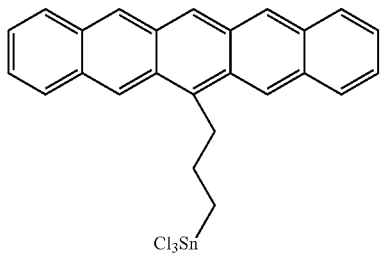

Finally, di-substituted stannous derivatives are also possible, as shown in formula V:

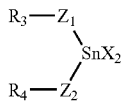

wherein
- R₃ and R₄ are independently selected from naphthalene, antracene, phenanthrene, pentacene or their substituted derivatives;
- Z₁ and Z₂ are optional hydrocarbon chains, independently selected from alkylene, alkenylene or alkynylene containing 1 to 10 carbons; and
- X is hydrolysable group.

Lastly, the following compound can be identified as an illustrative example of compounds according to formula I:

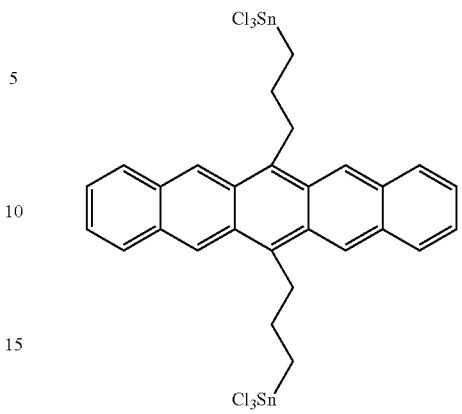

The novel monomers can be prepared by methods conventionally used in synthesis on metal-organic compounds. Thus, the Grignard reaction is one preferred way of proceeding; it involves the reaction of a halogenide of the organic compound with magnesium in order to form a reagent having the formula RMgHal, in which R has the same meaning as above and Hal stands for a halogen, in particular bromo or iodo. The Grignard reagent is then reacted with a tin halide. As discussed in the synthesis example below, the reaction can be carried out without external heating in the first stage. The reaction is brought to completeness at refluxing conditions. The total reaction time is about 10 to 20 hours.

The present monomers are suitable precursors for valuable polymer materials.

The polymerization synthesis is based on hydrolysis and condensation chemistry synthesis technique. The deposition of the material can be performed, for example, from aqueous liquid phase. However, the material can be deposited from various other processing solvents when made stable by fixing the conditions (such as pH-value of the solution) to keep the hybrid metal oxide material stable in solution.

When the monomers are polymerized, a tin oxide material will be obtained which has a repeating —Sn—O—Sn—O— backbone, with the polycyclic groups attached to the tin atoms. However, the backbone may be interrupted by organic groups, e.g. by polycyclic groups. The degree of cross-linking of the polymerized material depends on the precursors used. Generally, organo-tin compounds having three leaving groups, in particular three halo groups, will give rise to a higher degree of cross-linking than organo-tin compounds with two leaving groups. Cross-linking will also take place via substitutent groups attached to the organic moieties.

The polymerized material will have a molecular weight of about 500 to 500,000 g/mol, typically about 1000-30,000 g/mol. The higher the molecular weight, the thicker layer is obtained at the same dilution of the spinning liquid.

Polymerization can be carried out in melt phase or in liquid medium. The temperature is in the range of about 20 to 200° C., typically about 25 to 160° C., in particular about 80 to 150° C. Generally polymerization is carried out at ambient pressure and the maximum temperature is set by the boiling point of any solvent used. Polymerization can be carried out at refluxing conditions. It is possible to polymerize the instant monomers without catalysts, as disclosed in the example below, or by using acidic or alkaline catalysts.

The precursors used for polymerization are selected from the above monomers. in the presence of water can be dissolved in a solvent, such as PGMEA (propylene glycol monomethyl ether acetate), and spin or spray coated onto a substrate, such as a glass, silicon, metal, plastic or ITO (Indium Tin Oxide) surface.

The present monomer and polymers are useful for electronic and optical applications, such as for manufacturing of electroluminescent and spectral filtration devices. In particular they offer better selectivity for spectral filtration, electrical work function and photoemission excitation wavelength. They can be also used as one of thin film components in organic light emitting devices, organic solar cells and organic photodiodes than they silicon oxide based counter-parts. Furthermore, they may actually form single layer thin films components that can function as hybrid organic light emitting devices that can be further utilized in electro-luminescent displays. The index of refraction of the above-mentioned compositions, is relatively high: it is higher that of 2.0 for wavelengths in the range of 630 to 1550 nm. These types of materials are well suited for use as parts of a structure in an emissive component which transparent electrode(s) also exhibit(s) high index of refraction. Thus, harmful interface reflections are minimized.

In summary, the present materials have a great number of interesting new applications. Examples include:
A. Optical and electrical coatings
B. High dielectric constant (high-k) gate oxides and interlayer high-k dielectrics
C. ARC (anti-reflection) coatings
D. Etch and CMP stop layers
E. Protection and sealing (OLED etc.)
F. Organic solar cells
G. Optical thin film filters
H. Optical diffractive gratings and hybrid thin film diffractive grating structures
I. High refractive index abrasion resistant coatings.

The following non-limiting examples illustrate the present invention:

MONOMER EXAMPLE I

Mg (4.89 g) was placed in a round bottom flask. Two small spoons of granulated $I_2$ granules were added to the flask. The reaction mixture was stirred at room temperature for 30 minutes. Bromonaphthalene (23.2 ml) was added by a syringe through a needle into the flask. Also 2 drops of 1,2-dibromoethane were added. The reaction mixture was stirred at room temperature for 45 min. 87 g of $SnCl_4$ was added using a syringe and a needle into the reaction flask. 30 ml of $Et_2O$ was added to the flask in small portions. Immediately after the first portion, the reaction mixture became warmer. The temperature rose until the reaction mixture was slightly refluxing. The reaction mixture was allowed to reflux at 75° C. for 12 hours. 160 ml of toluene was added to "extract" the material from the round bottom flask. The solution was transferred with syringe via a needle to another round bottom flask. Unreacted $SnCl_4$ and toluene were removed by distillation and a material product was obtained. The material was then further purified by distillation.

Mass spectra measurements (Micromass LCT, ESI+, capillary: 3000V, sample cone: 35V, solvation temp: 150° C., source temp: 120° C.) were performed on the synthesized product to confirm the successful synthesis of naphthalene trichlorotin.

POLYMER EXAMPLE I 7.84 g of naphthalene trichlorotin was weighed into a round bottom flask and dissolved in 36.06 g of dichloromethane (DCM). Another solution containing DCM:$H_2O$ (1:8) suspension (5 ml:31 ml) was placed to a round bottom flask in an ice-bath. The naphthalene trichlorotin:DCM solution was added slowly to DCM:$H_2O$ solution by using dropping funnel. After addition, reaction mixture was stirred at room temperature for 145 min. Reaction mixture was placed to a separation funnel. 406 g of DCM and 50 ml of deionized water were added to the separation funnel. DCM and $H_2O$ layers were let to separate. After separation of the layers the DCM layer was filtrated using a filter paper. After filtration the solvent (DCM) was removed using a rotavapor (12 mbar, 40° C. bath temp, 30 min) followed by a high vacuum step (3 mbar, at room temperature). 3.67 g of clear material was obtained. The synthesized polymer was dissolved in 3.67 g of propylene glycol monomethyl ether acetate (PGMEA) and mixed over night. After filtration the material was ready for processing.

Polymeric naphthalene tin oxide polymer in PGMEA (POLYMER EXAMPLE I) was spin coated with 2000 rpm on a p-type silicon substrate. The sample was first baked at 150° C. for 5 minutes in air using a hot plate and then further for 1 hour in an oven at 200° C. under nitrogen flow. The final film thickness was ~50 nm and the refractive indices were 2.279, 2.171 and 2.090 at 632.8 nm, 850 nm and 1550 nm, respectively.

The invention is not limited to using a Grignard reaction for polycyclic aromatic group coupling to tin precursor as described in the MONOMER EXAMPLE I, but also Friedel-Craft synthesis can be applied when for example vinyl containing chlorotin compounds are used as precursors. Furthermore, the synthesis in the MONOMER EXAMPLE I is not limited of $SnCl_4$ usage as precursor, but also tin alkoxides can be applied as starting material. Polycyclic aromatic organo-tin components can be also co-polymerized mixed with each other or with organo-tin components known by prior-art, such as phenyl trichlorotin or divinyl dichlorotin. Sometimes co-polymerization with other hydrolysable metal or metalloid molecules, such as antimony chlorides, may be beneficial to introduce charge-transferring vacancies to the backbone matrix. Concentration of vacancies forming components may range 0.1-50 atomic-% or more preferably 1-10 atomic-%. Also other comonomers, for example indium compounds, which impart preselected properties of conductivity or other compounds, such as titanium compounds, for imparting properties of high refractive index, can be employed.

POLYMER PROPERTIES

Table 1 presents the refractive indices for naphthalene trichlorotin and naphthalene trichlorosilane based polymers. These two polymers were made from 100 mole-% of the respective precursor and cured at 200° C. under nitrogen flow.

As will appear from the data, refractive indices are significantly larger for naphthalene trichlorotin at all measured wavelengths, which make it more useful for applications wherein high refractive index is required.

TABLE 1

Refractive indices of polymers derived from naphthalene tricholoro tin and naphthalene trichlorosilane

| Wavelength | Naphthalene trichlorotin | Naphthalene trichlorosilane |
|---|---|---|
| 632.8 nm | 2.279 | 1.644 |
| 850 nm | 2.171 | 1.629 |
| 1550 nm | 2.090 | 1.618 |

While the present invention has been illustrated and described with respect to a particular embodiment thereof, it should be appreciated by those of ordinary skill in the art that various modifications to this invention may be made without departing from the spirit and scope of the present invention.

What is claimed is:

1. A polymer comprising units derived from an organo-tin compound having the formula I:

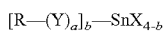   I wherein
R stands for a polycyclic hydrocarbyl residue which optionally
carries one or several substituents;
Y stands for a bivalent linker group;
X represents a hydrolysable group;
a is an integer 0 or 1; and
b is an integer 1 or 2.

2. The polymer according to claim 1, wherein
R is selected from fused polycyclic hydrocarbon comprises 2 to 6 alicyclic heterocyclic or aromatic rings having 5 to 7 members;
Y is an alkylene, alkenylene, or alkynylene chain comprising 1-10 carbons; and
X stands for halogen, alkoxy or hydrogen.

3. The polymer according to claim 1, wherein R and Y are independently substituted by one or several substituents selected from fluoro, bromo, $C_{1-10}$-alkyl, $C_{1-10}$-alkenyl, $C_{6-18}$-aryl, acryl, epoxy, carboxyl and carbonyl groups.

4. The polymer according to claim 1, wherein R stands for an unsubstituted or substituted fused hydrocarbon ring system selected from naphthalene, antracene, phenanthrene, and pentacene.

5. The polymer according to claim 1, wherein the compound comprises the formula II:

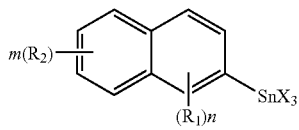

wherein
X is hydrolysable group,
$R_1$ and $R_2$ are independently selected from hydrogen, fluorine,
bromine, $C_{1-10}$-alkyl, $C_{1-10}$-alkenyl, $C_{6-18}$-aryl, acryl, epoxy, carboxyl and carbonyl groups, two substituents $R_1$ being capable of forming a 5 to 7 membered ring together with the adjacent carbon ring atoms to which they are attached;
m is an integer 0 to 4; and
n is an integer 0 to 3.

6. The polymer according to claim 5, wherein the compound is selected from
naphthalene trichlorotin having the formula IIa

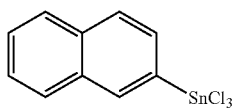

naphthalene trimethoxytin having the formula IIb

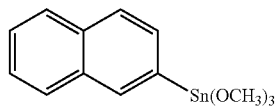

naphthalene triethoxytin:

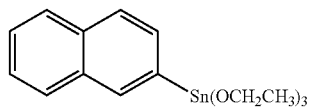

1,4-diphenyl naphthalene 3-trichlorotin having the formula

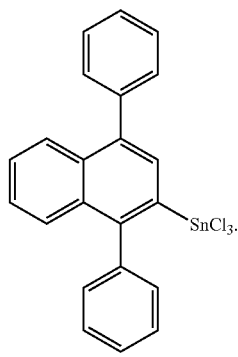

7. The polymer according to claim 1, wherein the compound comprises
a) a compound having the formula III:

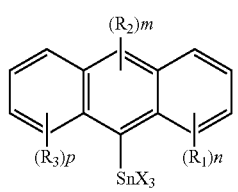

wherein X, $R_1$ and $R_2$ have the same meaning as in claim 5, $R_3$; stands independently of $R_1$ and $R_2$ for hydrogen, fluorine, bromine, $C_{1-10}$-alkyl, $C_{1-10}$-alkenyl, $C_{6-18}$-aryl, acryl, epoxy, carboxyl and carbonyl, m is 0 or 1, n is an integer 0 to 4 and p is an integer 0 to 4, and
b) or corresponding phenantrene derivatives thereof.

8. The polymer of claim 7, wherein the compound is selected from the group of compounds having the formulas

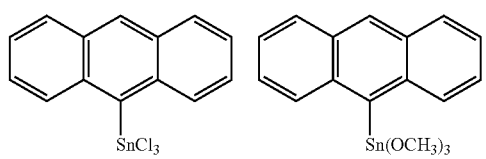

-continued

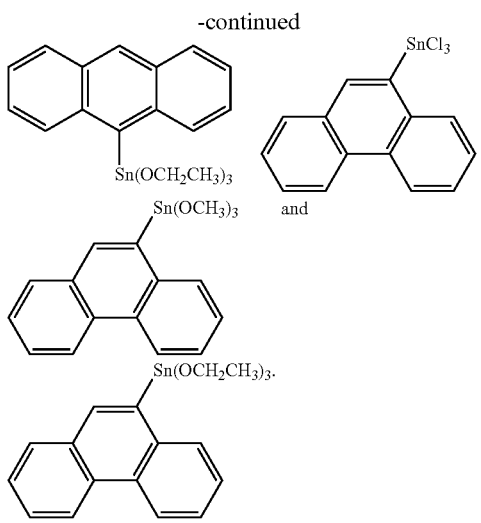

9. The polymer according to claim 1, wherein the compound comprises the formula IV:

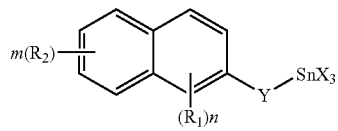

wherein

X is hydrolysable group;

Y is a bivalent linker group;

$R_1$ and $R_2$ are independently selected from hydrogen, fluorine, bromine, $C_{1-10}$-alkyl, $C_{1-10}$-alkenyl, $C_{6-18}$-aryl, acryl, epoxy, carboxyl and carbonyl groups, two substituents $R_1$ being capable of forming a 5 to 7 membered ring together with the adjacent carbon ring atoms to which they are attached;

m is an integer 0 to 4; and n is an integer 0 to 3.

10. The polymer of claim 9, wherein the compound is selected from the group of compounds having formulas

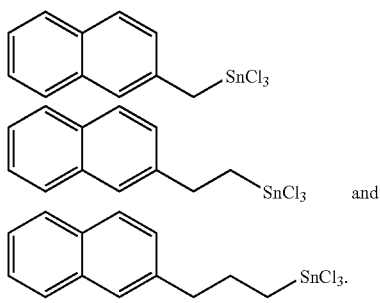

11. The polymer according to claim 1, wherein the compound is selected from the group of compounds having formulas

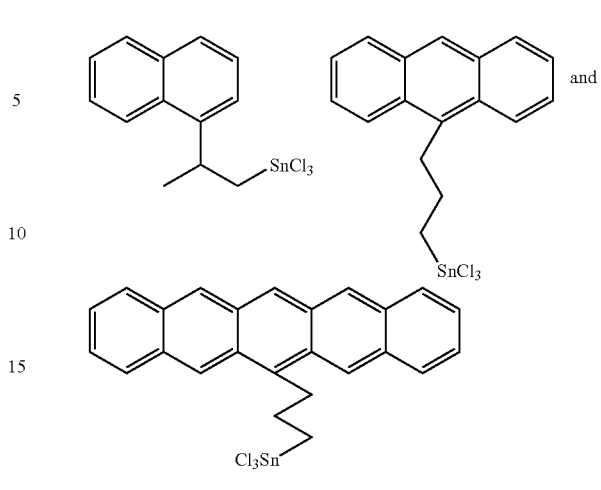

12. The polymer according to claim 1, wherein the compound comprises the formula V:

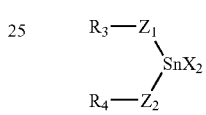

wherein $R_3$ and $R_4$ are independently selected from naphthalene, antracene, phenanthrene, pentacene or their substituted derivatives;

$Z_1$ and $Z_2$ are optional hydrocarbon chains, independently selected from alkylene, alkenylene or alkynylene containing 1 to 10 carbons; and X is hydrolysable group.

13. The polymer according to claim 1, comprising

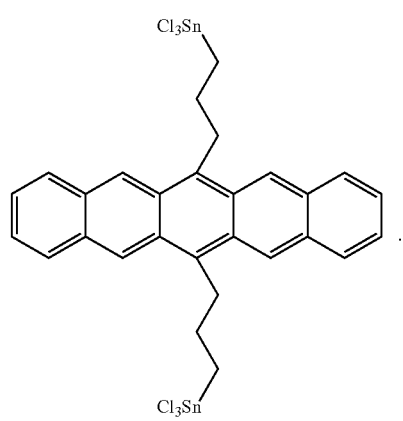

14. The polymer according to claim 1, comprising a tin oxide material having a refractive index in excess of 2.0 for wavelengths in the range of 630 to 1550.

15. The polymer according to claim 1, exhibiting a molecular weight of 500 to 500,000 g/mol.

16. A method of coating substrates, comprising the steps of:

applying on the surface of the substrate a solution of an organo-tin compound having the formula I according to claim 1, forming a thin layer on the surface,
removing the solvent of the solution and
subjecting the film to heat processing in order to cure the thin layer into a film.

17. A method for preparing the polymer of formula I, comprising the steps of:
reacting a halogenide of a polycyclic hydrocarbon organic compound with magnesium in an organic solvent in order to form a reagent having the formula RMgHal, in which R has the same meaning as above and Hal stands for a halogen;
mixing the reagent with tin halide to form a reaction mixture;
reacting the reagent with the tin halide to form a compound of formula I in the reaction mixture;
recovering the compound of formula I from the reaction; and
polymerizing the compound of formula I to produce a polymer.

* * * * *